(12) United States Patent
Betts

(10) Patent No.: US 8,206,391 B2
(45) Date of Patent: Jun. 26, 2012

(54) EXPANDABLE BLADE DEVICE FOR STABILIZING COMPRESSION FRACTURES

(75) Inventor: Andres Betts, San Clemente, CA (US)

(73) Assignee: Vertech, Inc., San Clemente, CA (US)

(*) Notice: Subject to any disclaimer, the term of this patent is extended or adjusted under 35 U.S.C. 154(b) by 701 days.

(21) Appl. No.: 12/025,629

(22) Filed: Feb. 4, 2008

(65) Prior Publication Data

US 2008/0221505 A1 Sep. 11, 2008

Related U.S. Application Data

(63) Continuation-in-part of application No. 11/836,731, filed on Aug. 9, 2007.

(60) Provisional application No. 60/893,556, filed on Mar. 7, 2007.

(51) Int. Cl.
*A61B 17/00* (2006.01)
(52) U.S. Cl. ............................................. 606/79; 606/80
(58) Field of Classification Search .................... 606/79, 606/80
See application file for complete search history.

(56) References Cited

U.S. PATENT DOCUMENTS

| 5,275,610 | A  | * | 1/1994  | Eberbach ..................... 606/198 |
| 5,591,170 | A  | * | 1/1997  | Spievack et al. ................ 606/82 |
| 6,152,894 | A  | * | 11/2000 | Kubler ............................ 604/22 |
| 6,676,665 | B2 |   | 1/2004  | Foley et al. |
| 7,226,481 | B2 | * | 6/2007  | Kuslich ...................... 623/17.11 |
| 7,597,714 | B2 | * | 10/2009 | Suddaby .................... 623/17.16 |
| 2006/0004457 | A1 | * | 1/2006 | Collins et al. .............. 623/17.16 |
| 2007/0197861 | A1 |   | 8/2007 | Reiley et al. |
| 2008/0009875 | A1 |   | 1/2008 | Sankaran et al. |

* cited by examiner

*Primary Examiner* — Kevin T Truong
*Assistant Examiner* — David Bates
(74) *Attorney, Agent, or Firm* — Fish & Associates, PC

(57) ABSTRACT

A medical device and method of using the device to reinforce and stabilize a compressed tissue is disclosed. The medical device is inserted into the tissue, typically a vertebral bone, cuts the tissue inside, and then a binding cement is injected into the pulped tissue without removing the tissue. The medical device is designed to disrupt and pulp the tissue without exerting a compressive force against the walls by using thin blades that buckle away from the core, and by rotating the blades while expanding/contracting the blades at the same time.

11 Claims, 3 Drawing Sheets

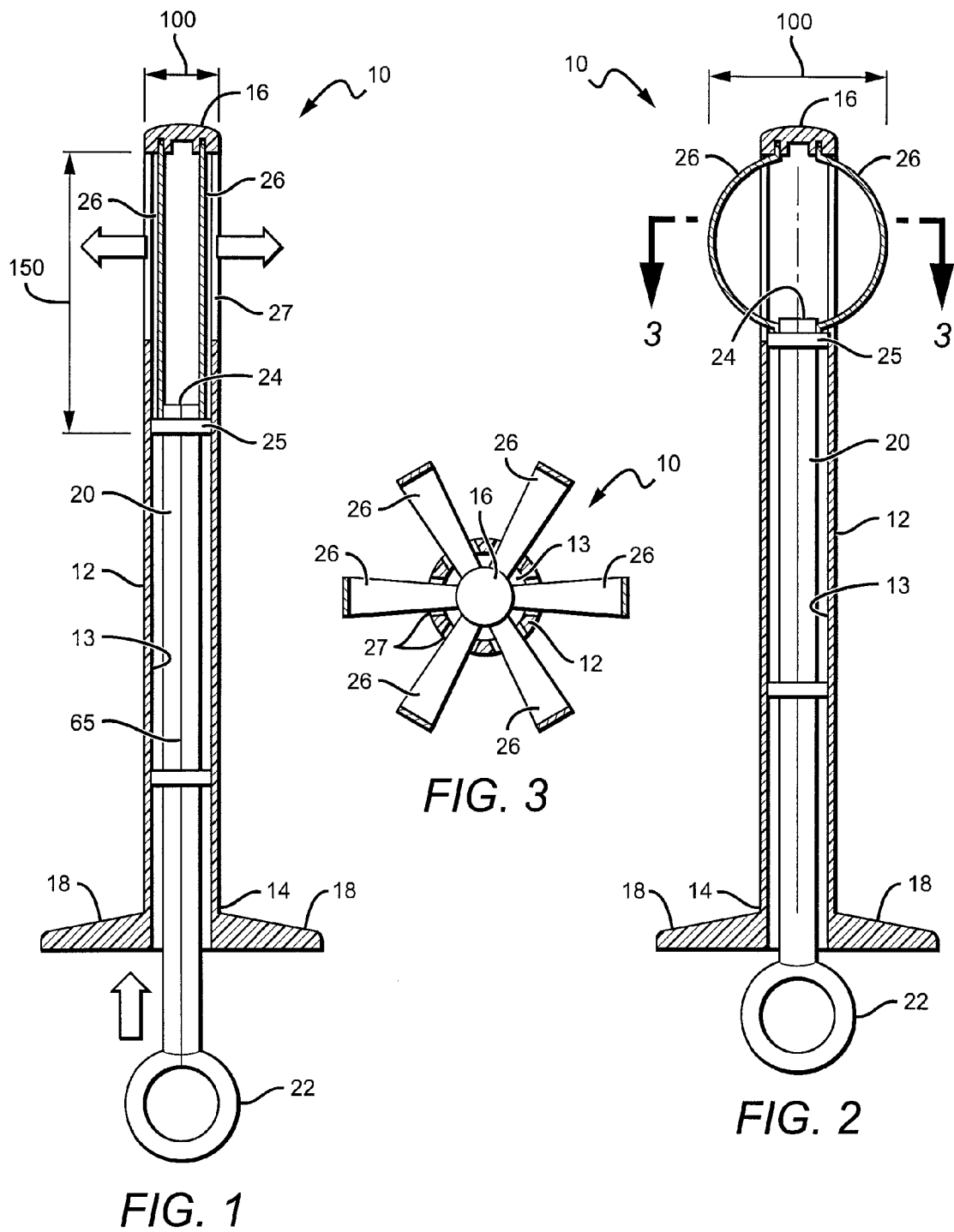

EXPANDABLE BLADE DEVICE FOR STABILIZING COMPRESSION FRACTURES

CROSS-REFERENCE TO RELATED APPLICATION

This application is a continuation-in part of patent application Ser. No. 11/836,731, filed on Aug. 9, 2007, which claims priority to provisional patent application Ser. No. 60/893,556, filed on Mar. 7, 2007, which are both hereby incorporated by reference in their entirety.

FIELD OF THE INVENTION

The field of the invention is tissue reinforcement surgery.

BACKGROUND OF THE INVENTION

Weakened tissue, especially bone, can cause multiple complications if it can not bear a certain threshold of weight. For example, compression fractures of the spine are a common, painful and debilitating complication of osteoporosis or neoplastic diseases of the vertebral bodies. In many patients, the pain is very severe and patients are unable to bear their own weight. This can require prolonged bed rest, which is known to lead to further complications including pneumonia, thromboembolism, muscle-decay, and further bone demineralization. In addition to being painful and debilitating, compression fractures of vertebral bodies also typically result in a loss of vertebral height along the anterior margin of the involved vertebrae. This leads to an anterior wedge deformity that causes the kyphosis. Patients having compression fractures of the spine are generally treated by a procedure called percutaneous Vertebroplasty.

Common Vertebroplasty procedures involve drilling into a vertebral cavity, removing tissue from within the cavity, and then delivering polymethylmethacrylate (PMM) cement or other physiologically acceptable binding material into the body of the fractured vertebra. For example, US 2007/0197861 to Reiley teaches using a rotatable loop and cutting blade to sever the tissue, and then uses a rotatable brush or a suction tube to remove material within a bone before adding PMM cement. US 2008/0009875 to Sankaran teaches using expandable, rotatable blades which are used to sever the interior tissue, but then injects a liquid into the cavity before sucking out the tissue. The process of removing the severed tissue can cause further trauma to the patient, and could cause the walls of the cavity to compress and seal, decreasing the areas where the PMM could interdigitate with the uncut tissue walls.

Reiley, Sankaran, and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Other methods of restoring a vertebral height involve inflating a balloon within the cavity, or using another object to push against the cavity walls to restore a vertebral height. U.S. Pat. No. 6,676,665 to Foley teaches a surgical instrument that pushes against the interior of a cavity wall to restore a vertebral height. Such compression techniques, however, also cause the walls of the cavity to seal, decreasing the areas where injected PMM could interdigitate with the uncut tissue walls.

In view of the current state of the art, there is still a need in the art for tissue surgery apparatus and methods for reinforcing weakened tissue.

SUMMARY OF THE INVENTION

The present invention provides apparatus, systems, and methods in which a volume of tissue is disrupted, and then reinforced in situ with a physiologically acceptable binding material.

In especially preferred embodiments, little or none of the disrupted material is excised, although it is contemplated that some of the material could be permanently removed, or even removed and then replaced. It is less preferred embodiments, larger amounts of the disrupted tissue could be removed and/or replaced, including up to 10 wt %, 20 wt %, 30 wt %, 40 wt %, 50 wt %, etc.

It is also preferred that the disrupting process does not appreciably compress tissues adjacent the disrupted tissue, as for example would occur with a Kyphoplasty.

The tissue is generally disrupted using a medical device with a plunger that has a blade, and with a manipulator functionally coupled to the plunger that has a first mechanism that can extend the blade.

The plunger can have more than one flexible blade that buckles from the plunger's core as the plunger squeezes two portions or positions of the blades towards one another. Typically, the ends of the blades are squeezed towards one another, and the positions that are squeezed can be more than 5 mm or 10 mm apart to enable the blades to extend farther from the core. Preferably, the blades can extend at least 10 mm from the plunger core. The blades are preferably flat, with have an average width of no more than 5 mm or 3 mm to minimize displacement of the disrupted tissue. Contemplated blades also include strong wire filaments or loops that slice through the tissue. Especially preferred blades have a width of 2-3 mm. Unless the context dictates otherwise, all ranges herein are to be deemed inclusive of their endpoints.

The manipulator can have a second mechanism that rotates the blades around the axis, but preferably the same mechanism rotates and extends the blades. In an exemplary embodiment, the mechanism rotates and extends the blades at the same time, and retracts and rotates the blades at the same time. The simultaneous rotation and extension/retraction of the blades allows the blades to slice through the tissue while minimizing the amount of tissue displaced by the blade movement.

Preferably, the plunger's distal end is no more than 5 mm in width or diameter and has a channel that is suitable for carrying a physiologically acceptable binding material into the disrupted tissue.

To reinforce a weakened tissue, a skilled physician can insert the distal end of the claimed medical device, or another device with similar functionality, into a tissue. The physician disrupts a volume of the tissue with the device and injects a physiologically acceptable binding material into the disrupted volume of tissue, all without permanently removing or displacing at least 50 wt % of the disrupted volume.

Typically the distal portion of the device is inserted through a cortex of a bone. A blade is then extended and rotated from that distal portion to disrupt a volume of tissue. The blade is preferably extended and rotated concurrently, and is retracted and rotated concurrently to minimize the amount of tissue that is displaced. The rotation of the blade can introduce multiple lacerations into the volume of tissue, and/or can pulp the volume of tissue.

The physiologically acceptable binding material, for example PPM, is preferably injected directly into the disrupted volume of tissue. The binding material can be advantageously injected under pressure sufficient to interdigitate the material into the non-disrupted tissue, for example a lacerated tissue wall or an exposed trabecular bone. The physiologically acceptable binding material can be used to increase the height of a vertebral body, and thereby preferably restore the vertebral body to a normal, or at least more normal, anatomical height.

Various objects, features, aspects and advantages of the inventive subject matter will become more apparent from the following detailed description of preferred embodiments, along with the accompanying drawings in which like numerals represent like components.

BRIEF DESCRIPTION OF THE DRAWINGS

FIG. 1 is a partial cross-sectional view of an embodiment of a device of the present invention with its blades in a retracted position.

FIG. 2 is a partial cross-sectional view of the embodiment depicted in FIG. 1.

FIG. 3 is a top-down view of the embodiment depicted in FIG. 2.

DETAILED DESCRIPTION

Figure 4:
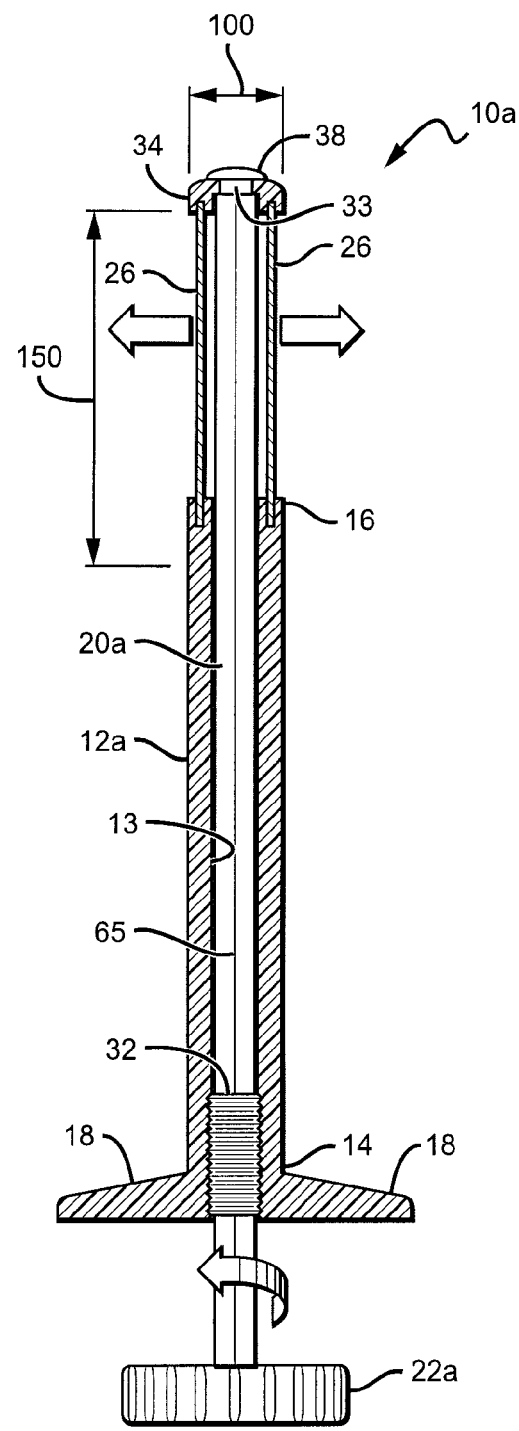
FIG. 4 is a partial cross-sectional view of an embodiment of a device of the present invention.

In the following paragraphs, the present invention will be described in detail by way of example with reference to the attached figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

A. Devices of the Present Invention

Referring now to the figures, which are illustrative of multiple embodiments of the present invention only and are not for purposes of limiting the same, FIG. 1 depicts an expandable blade device 10 constructed in accordance with one embodiment of the present invention. The expansion blade device includes a rigid housing 12 which defines a lumen 13. Preferably the housing 12 is roughly tubular, but it may be any suitable shape or configuration. Housing 12 may be any suitable material, such as a suitable polymer, plastic, metal, or alloy. In some embodiments, housing 12 may be flexible. The lumen 13 is preferably tubular, but it may be any suitable shape or configuration. In preferred embodiments, the device 10 of the present invention is insertable within a cannula 60 which has been placed within the injured vertebra. Preferably, cannula 60 is a large bore cannula between about eight gauge to about eleven gauge created within a cortex of a bone.

The housing 12 has a proximal end 14 and a distal end 16. Preferably, distal end 16 is closed. In some embodiments, proximal end 14 includes grip member 18 that may aid a user's ability to grip and/or manipulate device 10. In some embodiments, grip member 18 is located at proximal end 14, but grip member 18 may be located near proximal end 14 or at any suitable position on housing 12. In the depicted embodiment, grip member 18 is a pair of wings where each wing extends outwardly from proximal end 14 in opposed relation to the other. In such an embodiment, a user's index finger may be placed over one of the wings comprising grip member 18, while the user's middle finger may be placed over the other wing comprising grip member 18, similar to the handling of a syringe. In other embodiments, grip member 18 may be any suitable structure that may aid user's ability to grip and/or manipulate device 10, for example finger loops, depressions, grooves, or a textured surface.

As illustrated in FIGS. 1 and 2, plunger 20 is disposed within the lumen 13 of housing 12 such that plunger 20 is movable relative to housing 12. Similar to housing 12 and lumen 13, plunger 20 may be any suitable diameter and length. In preferred embodiments, plunger 20 has a diameter slightly less than lumen 13 such that plunger 20 is movable along the axis of the housing, but exhibits little, if any, movement transverse to the axis of the housing. In some embodiments, plunger 20 may be equipped with a structure or structures that facilitate its movement within the lumen 13. In some embodiments, plunger 20 may be flexible.

A manipulator 22 is located at or near the proximal end of plunger 20. Manipulator 22 may be any structure suitable to permit the user to move plunger 20 relative to housing 12. In some embodiments manipulator 22 may be a loop a lever, handle, or dial. In preferred embodiments, manipulator 22 is connected, directly or indirectly, to plunger 20 and blades 26 such that force acting upon blades 26 is transferred to manipulator 22. Accordingly, in preferred embodiments, the user of device 10 is provided with a tactile feel.

Attached to the distal portion of plunger 20 is a plurality of blades 26. The use of multiple blades, as opposed to a single blade, allows for more surface area to contact the vertebral endplate and promotes more reliable fluoroscopic imaging in multiple planes. Each blade 26 may have any suitable width and each blade 26 in a given device need not have the same width. In some embodiments the blades 26 may have a width of from about 0.5 mm to about 10 mm. Preferably, each blade 26 has a width of from about 2 mm to about 3 mm, although smaller wire blades (where the effective width is the diameter of the wire) are also contemplated. Wire blades are thought to be advantageous in that they could cut through the tissue as the blades rotate, without pushing the tissue radially as a thicker blade or a Kyphoplastic operation would tend to do. The blades 26 are disposed substantially parallel to the axis of housing 12 and do not protrude past the outer surface of housing 12 in their unexpanded state. Each blade 26 may be composed of any suitable material that can cut or shave trabecular bone and is resilient. In some embodiments, blades 26 may be made of any compliant polymer, plastic, metal or alloy. Preferably, blades 26 are made of metal. Embodiments of the invention may feature any number of blades 26. In some embodiments there may be 1, 2, 3, 4, 5, 6, 7, 8, 9, or 10 blades. In a preferred embodiment, there are six blades 26. In another preferred embodiment, there are two blades 26.

In some embodiments, the distal portion of housing 12 has a plurality of slots 27. Preferably the slots 27 are located close to the distal end 16. The slots 27 maybe any shape and size so long as they do not impede radial expansion of the blades 26. In the illustrated embodiment, the slots 27 are elongate rectangular in shape.

Blades 26 are disposed such that when manipulator 22 is moved in a certain manner, the blades 26 will expand radially from the axis of the housing. In some embodiments, this is achieved by translating the distal movement of plunger 20 along the axis of housing 12, for example as depicted in FIG. 2, in to the expansion or flexing of blades 26 radially away from the axis of the housing 12 and through slots 27. In the illustrated embodiments such movement is achieved by attaching the proximal ends of blades 26 to plunger 20 and attaching the distal ends to housing 12.

Blades 26 may be attached to plunger 20 and housing 12 in any suitable manner, including indirectly. In some embodiments, blades 26 may be attached by welding, crimping, or with screws, rivets, or adhesives. The blades 26 may be attached to any suitable location of the plunger 20 and housing 12. Preferably, the proximal ends of blades 26 are attached in proximity to the distal end 24 of plunger 20 and the distal ends of blades 26 are attached to an interior surface of the housing 12 at the distal end 16. In a preferred embodiment, the proximal ends of blades 26 are each attached to a shoulder portion 25 of the plunger 20 which is located proximally to the distal end 24 of plunger 20.

The disposition of the blades 26 is also such that a diameter 100 of the blades 26 in the expanded configuration is variable. FIG. 1 illustrates an embodiment where blades 26 are not expanded radially outward, whereas FIG. 2 illustrates an embodiment that where the blades 26 are expanded to the maximum diameter. Although not depicted, the user may vary the extent of the expansion of the blades 26 and thereby vary the diameter 100 between the maximum and the unexpanded states. The user varies the diameter by varying the movement of the plunger 20 relative to the housing. The user may control this movement by acting upon the manipulator 22 and moving the manipulator 22 with respect to grip member 18. Accordingly, for example, in FIGS. 1 and 2 the user's movement of the manipulator 22 toward the distal end 16 of housing 12 moves plunger 20 toward the distal end 16 of housing 12. In turn, the movement of plunger 20 moves the proximal end of blade 26 toward the distal end of blade 26, thereby expanding blade 26 radially from the axis of housing 12. FIG. 3 depicts device 10 from a top-down perspective, with the blades 26 being in a fully deployed state illustrated in FIG. 2. As is illustrated in FIG. 3, each blade 26 protrudes through a slot 27 disposed within the rigid housing 12. In some such embodiments, the distance of the movement of plunger 20 toward the distal end of housing 12 controls the amount of expansion of blade 26 and the diameter 100. In a preferred embodiment, the maximum diameter between blades is about 2 cm. In some embodiments manipulator 22 is configured to display or otherwise notify the user of the cutting diameter of the blades 26. For example, manipulator 22 or the distal portion of plunger 20 may have markings showing the extent of radial expansion of blades 26 achieved by a certain movement of manipulator 22.

While the blades may be biased in any suitable manner, or not biased at all, the blades are preferably biased to return to a straight configuration when no force is applied to plunger 20. Blades 26 have shape memory properties, and are biased to return to their unexpanded position shown FIG. 1. In such embodiments, the blades 26 will remain expanded only so long as the user applies force to the manipulator 22 (and thereby to plunger 20). In alternative embodiments, the manipulator 22 is configured such that the user need not apply continuous force to maintain the expansion of blades 26. In some such embodiments, the blades 26 may be maintained in a fully or partially expanded state through the use of a clamp, or some other fastening means (not shown) that is operable to maintain the plunger 20 in a prescribed position relative to the housing 12.

In some embodiments, device 10 may also have a guide wire engaging member 65 that functions to engage a structure that aids the insertion or other movement of device 10 within the body. In some embodiments, the guide wire engaging member 65 is within a hollow device 10 extending from its distal end 16 to the manipulator 22 (as depicted in FIG. 1). In such an embodiment, plunger 20 would be hollow, as would manipulator 22 and distal end 16.

Figure 5:
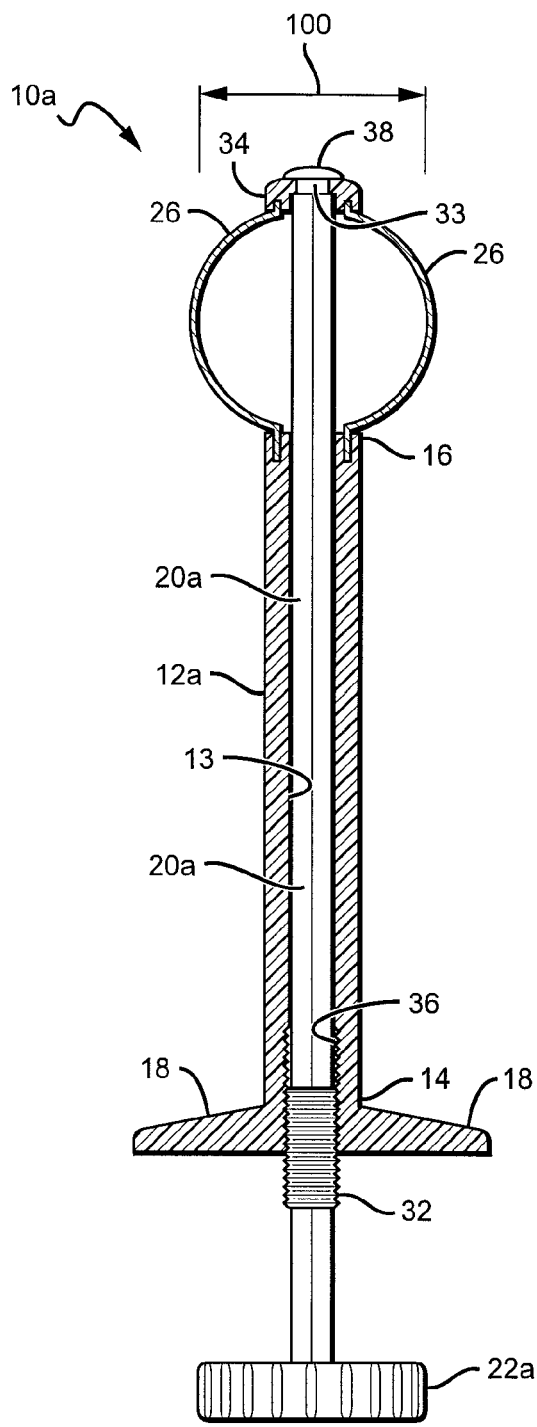
FIG. 5 is a partial cross-sectional view of the embodiment depicted in FIG. 4.

FIGS. 4 and 5 depict an alternative embodiment of a device of the present invention, device 10a. Similarly to the device 10 depicted in FIGS. 1 and 2, device 10a comprises a housing 12a having a proximal end 14 and a distal end 16, a grip member 18 (depicted as a pair of wings), lumen 13 and blades 26. Device 10a may also have guide wire engaging member 65 (as illustrated in FIG. 4). The depicted embodiment works in a manner similar to the embodiment depicted in FIGS. 1 and 2, but, among other differences, utilizes a manipulator 22a, housing 12a, and configuration of plunger 20a that are different than those in the embodiment depicted in FIGS. 1 and 2.

In the embodiment depicted in FIGS. 4 and 5, a proximal portion of the interior surface of the housing 12a has a threaded region 36. Similarly, a proximal portion of plunger 20a has a threaded region 32. The threaded portion 32 is threadably engaged to the internally threaded portion 36 of the housing 12a. As such, rotation of plunger 20a causes movement of plunger 20a along the axis of housing 12a. Housing 12a does not extend to the distal end of the device 10a in this embodiment. Distal end 16 is near the proximal end of blades 26. Blades 26 are attached at their proximal end to housing 12a and at their distal end to sleeve 34. Sleeve 34 is rotatably connected to plunger 20a is an annular sleeve 34 which partially resides within a continuous, circumferentially extending groove 33 which is disposed in close proximity to distal end 38 of plunger 20a. Sleeve 34 is capable of rotation relative to the screw unit 28 when the plunger 20a is rotated relative to the housing 12a.

Manipulator 22a in the depicted embodiment is a handle portion that extends radially from the axis of housing 12a. In this embodiment, manipulator 22a is configured to allow the user to grasp and rotate manipulator 22a and, thereby rotate plunger 20a. Of course, manipulator 22a can have any configuration capable of rotating plunger 20a relative to housing 12a. In the depicted embodiment, blades 26 are extended by counter-clockwise rotation of manipulator 22a which, in turn, causes counter-clockwise rotation of plunger 20a relative to housing 12a. In such an embodiment, the counter-clockwise rotation of manipulator 22a moves manipulator 22a away from the housing 12a, thereby causing plunger 20a to move proximally along the axis of housing 12a. Such movement decreases the distance between the distal end 16 of housing 12a and the distal end 38 of plunger 20a to decrease. Since the blades 26 are resilient and flexible and attached to the distal end 38 of plunger 20a and near the distal end 16 of housing 12a, this decrease in distance forces the blades 26 to expand or flex (and hence deploy) radially from the axis of housing 12a in the manner illustrated in FIG. 5. Conversely, in the depicted embodiment, when manipulator 22a and plunger 20a are rotated in a clockwise direction, the distance between the distal ends 16 and 38 is effectively increased, causing the blades 26 to return to the initial, unexpanded position illustrated in FIG. 4. Like in device 10, the blades 26 of device 10a10a may be partially expanded or deployed to a state lying anywhere between the extremes illustrated in FIGS. 4 and 5 by selective variation in the degree of rotation of manipulator 22a.

Of course, one of skill in the art will appreciate that the device could be configured such that counter-clockwise movement contracts the blades 26 and clockwise movement expands the blades 26. Blades 26 simultaneously cut through tissue and expand radially from the axis of housing 12a at in a predictable controlled manner since manipulator 22a follows the track of threaded region 36. As a result, blades 26 cut tissue in spirally without exerting an outwardly radial, compressive force adjacent the disrupted tissue, as for example would occur with a Kyphoplasty or a thick blade that extends radially. Of course, thinner threads would tend to cut in a tighter spiral than thicker threads. It should also be appreciated that housing 12a can be rotated before rotating manipulator 22a counter-clockwise to contract blades 26 to cut the tissue along a separate spiral. By rotating manipulator 22a clockwise, rotating housing 12a a quarter turn, and then rotating manipulator 22a counter-clockwise, an operator can easily and efficiently pulp a relatively large volume of tissue.

In some embodiments, the configuration of the screw mechanism is such that blades 26 will remain in a particular expanded state even though the user is not applying force to manipulator 22a. Accordingly, the blades 26 can be maintained in the deployed position without continuous application of force by the user and without the need for any ancillary clamping or similar device. In such embodiments blades 26 will remain until plunger 20a is rotated in a clockwise manner and blades 26 are returned to their initial unexpanded position.

In those instances when the user wants to rotate device 10 in its entirety, the user may simultaneously rotate the housing 12a and plunger 20a. In another embodiment, such rotation may be assisted through the use of a clamp (not shown), or other fastening device or configuration operative to lock plunger 20a in place relative to the housing 12a. In this case, when the clamp is locked, device 10a may be rotated in its entirety by either rotating the plunger 20a (or manipulator 22a) or the housing 12a, without the user ensuring that the two are simultaneously rotating.

B. Methods of the Present Invention

In addition to the devices described above, the present invention also includes methods of using the devices of the present invention and any other suitable device.

Figure 6:
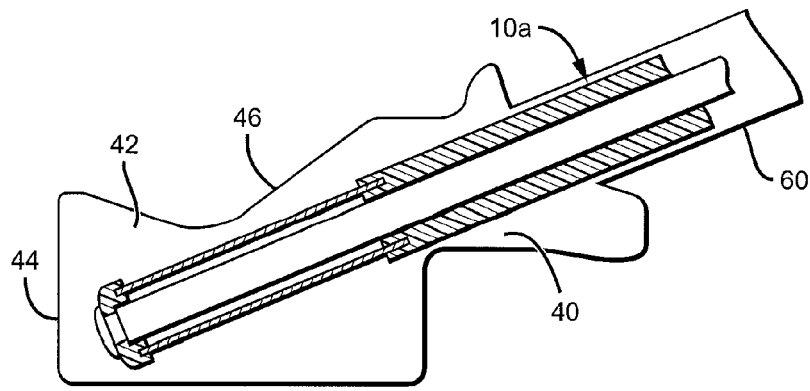
FIG. 6 is a partial side view illustrating an exemplary positioning of an embodiment of a device of the present invention within the vertebral body, wherein the blades of the device are in 11 retracted position.
Figure 7:
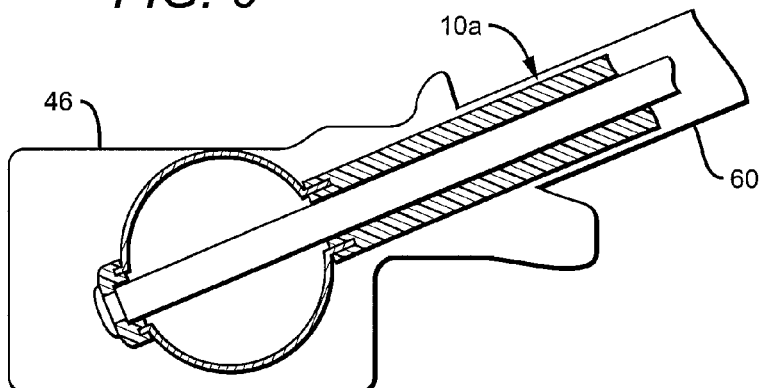
FIG. 7 is a partial side view illustrating the positioning of an embodiment of a device of the present invention, wherein the blades are in a deployed position and the vertebral height has been restored.
Figure 8:
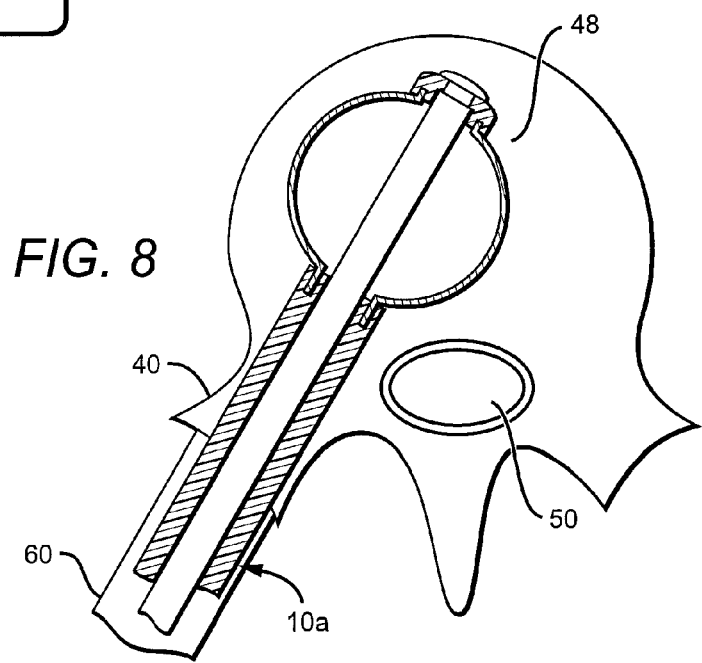
FIG. 8 is a top-down view of an exemplary positioning of an embodiment of a device of the present invention within the vertebral body, wherein the device entered the vertebral body via the pedicle while avoiding the spinal canal.

FIGS. 6-8 depict an embodiment of a method of the present invention useful to stabilize a vertebra fracture while also restoring the vertebral height. As depicted, the method uses device 10a, but any suitable device may be used, including device 10 and any other embodiment of the devices of the present invention.

The method initially involves getting access to the interior volume of vertebral body 42. In some embodiments, this is done by percutaneously inserting a cannula 60. In other embodiments, an open procedure may be used to get access to the interior volume of vertebral body 42. Cannula 60 may be any structure suitable for providing access to vertebral body 42 and can be made of any suitable material. Preferably, cannula 60 is a hollow tube having a diameter slightly larger than the diameter of the device used in the procedure. In any event, the exterior surface of vertebral body 42, for example a cortex of a bone, is drilled, cut, or otherwise compromised to permit access to the internal volume. Such may be achieved by any suitable method and with any suitable device.

The interior volume of vertebral body 42 can be accessed at any suitable position. In some embodiments, access may be through a side of vertebral body 42. In other embodiments, access may be through the posterior of vertebral body 42. In preferred embodiments, access to the internal volume of vertebral body 42 is through the pedicle 40. As depicted in FIG. 8, by inserting cannula 60 into the vertebra body 42 through the pedicle 40, the user is better able to avoid penetrating the spinal canal 50, thereby preventing potentially permanent damage and paralysis to the patient. In some embodiments, the location of cannula 60 may be visualized by any suitable imaging technique, including those known in the art. Preferably, visualization is by fluoroscopic imaging techniques.

After gaining access to the internal volume of vertebral body 42, device 10a is inserted into that internal volume. In preferred embodiments, device 10a is inserted into and advanced through cannula 60. In preferred embodiments, device 10a is inserted into the cannula with the blades 26 in an unexpanded state. In other embodiments, blades 26 may be expanded to some extent, so long as blades 26 do not prevent insertion of the device 10a into cannula 60 or into vertebral body 42. The device 103 is advanced through the cannula so that the blades 26, 26 protrude beyond the distal end of the cannula 60 and into the internal volume of vertebral body 42. In preferred embodiments, device 10a is moved or manipulated until blades 26 are near the anterior surface 44 of the vertebral body 42 as depicted in FIG. 6. In some embodiments, the extent of insertion of device 10a is monitored using a suitable imaging technique.

When the device 10a is properly positioned within the vertebral body 42, the blades 26 are expanded radially as needed to contact superior endplate 46. The expansion of the blades 26 may be done by any suitable method, including those described herein. For example (and with reference to FIGS. 4 and 5), in the case of device 10a, the blades 26 may be expanded by rotating manipulator 22a counter-clockwise relative to housing 12a, thereby causing plunger 20a to rotate counter-clockwise and decreasing the distance between the distal ends 16, 38. Blades 26 are expanded such that they apply force to superior endplate 46 until the superior endplate 46 has been displaced into a desired position. In preferred embodiments, the desired position for superior endplate 46 is the normal anatomical position for the particular patient, for example as depicted in FIG. 7. Although the normal anatomical position of superior endplate 46 may be different for each patient or even each vertebrae of each patient, a preferred method, which will properly position the superior endplate 46 for many patients, contemplates expanding blades 26 to a diameter of about zero.

In one embodiment, where the blades 26 are thin wires (1-3 mm dia.), the blades 26 are first rotated to cut a volume of tissue, and then are periodically rotated and slightly expanded to create lacerations in the tissue wall to help the physiologically acceptable binding material interdigitate with the tissue wall. In another embodiment, an outer surface of blades 26 is roughened to introduce multiple lacerations into the volume of tissue.

In a preferred embodiment, the blades 26 are made of metal and are easily visualized using fluoroscopic methods. However, various other imaging techniques and methods, some capable of visualizing blades 26 that are not made of metal, may be used in other embodiments. However achieved, visualization of the blades 26 aids the user in expanding blades 26 as needed to achieve the desired orientation of the superior endplate 46. Visualization may also aid the user in performing other aspects of the methods of the present invention. In some embodiments, the force of contact between blades 26 and superior endplate 46 is transmitted to the user of device 10*a* through the manipulator. In some such embodiments, this tactile feel aids the user in determining if and when superior endplate has been moved to the desired position. In further embodiments the immediate tactile feedback provided to the user is combined with the visual fluoroscopic imaging, resulting in restoration of the vertebral height with minimal risk of rupturing the vertebral body itself.

Expansion of the blades is also necessary for another aspect of the methods of the present invention that may be performed before or after the superior endplate 46 is restored-cutting, carving, shaving, or otherwise disrupting the volume of the trabecular bone 48 in the internal volume of vertebral body 42. In preferred embodiments, the trabecular bone 48 is cut, carved, or shaved, preferably in a manner that leaves the trabecular bone with texture and/or pores that may receive a physiologically acceptable binding material. In a preferred embodiment once the blades 26 are expanded and the superior endplate 46 has been restored to the desired position, device 10*a* is rotated in its entirety to carve out the trabecular bone 48 within the vertebral body 42, thereby creating a volume of disrupted tissue within the internal volume of the vertebral body 42.

The physiologically acceptable binding material may be instilled into the vertebral body by any suitable method using any suitable device. In one embodiment, device 10*a* is first removed and the physiologically acceptable binding material is instilled through the cannula 60 and into the vertebral body 42, as is known in the art. Preferably, the device has a channel that allows a user to inject physiologically acceptable binding material into the volume of disrupted tissue without having to remove the device, and without actively removing any of the disrupted tissue. Any amount of physiologically acceptable binding material sufficient to add stability to vertebral body 42 may be used. Preferably, physiologically acceptable binding material is added until the height of vertebral body 42 is increased, or is restored to a normal anatomical height. In preferred embodiments where trabecular bone 48 has been cut, carved, or shaved, the physiologically acceptable binding material is injected under a pressure sufficient to interdigitate with the exposed trabecular bone 48. In such embodiments, the interdigitation of the physiologically acceptable binding material and the trabecular bone 48 forms a bond that is capable of maintaining the restored vertebral height even after the subsequent placement of mechanical loading on the spine.

Once the superior endplate 46 has been restored to the desired position, device 10*a* is withdrawn from the interior volume of the vertebral body 42. Preferably, blades 26 are returned to their unexpanded state prior to removal of device 10*a*. As used herein, a physiologically acceptable binding material is any material suitable for placement in an internal portion of a bone in a human body and that is capable of providing stability and/or added strength to such a bone. Preferably, the physiologically acceptable binding material is also capable of interdigitating with internal surfaces of a bone, such as trabecular bone. Examples of physiologically acceptable binding materials include, but are not limited to, cements containing polymethylmetacrylate (PMM) and materials utilizing biological or synthetic bone. The referred physiologically acceptable binding material is a cement that contains PMM. In some embodiments, the physiologically acceptable binding material may contain additional substances, such as antibiotics or compounds that aid imaging of the physiologically acceptable binding material once it is added to the body. In some embodiments, the physiologically acceptable binding material may contain barium to aid fluoroscopic imaging of the physiologically acceptable binding material. It is seen that devices and methods are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in, this description may practice the invention as well.

While various embodiments of the present invention have been described above, it should be understood that they have been presented by way of example only, and not of limitation. Likewise, the various diagrams may depict an example configuration for the invention, which is done to aid in understanding the features and functionality that may be included in the invention. The invention is not restricted to the illustrated example configurations, but the desired features may be implemented using a variety of alternative configurations. Indeed, it will be apparent to one of skill in the art how alternative functional or physical configurations may be implemented to implement the desired features of the present invention. Additionally, with regard to operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one' "one or more" or the like; and adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping; but rather should be read as "and/or" unless expressly stated otherwise. Similarly, a group of items linked with the conjunction "or" should not be read as requiring mutual exclusivity among that group; but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

Additionally; the various embodiments set forth herein are described in terms of exemplary illustrations and figures. As will become apparent to one of ordinary skill in the art after reading this document, the illustrated embodiments and their various alternatives may be implemented without confinement to the illustrated examples.

Thus, specific embodiments and applications of reinforcing a tissue have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method comprising the steps of:
    inserting a distal portion of a device into a tissue by passing through a cortex of a bone;
    disrupting a volume of the tissue by extending at least one blade parallel to the axis of the device through the cortex and into the tissue, bending the blade convexially from the axis of the device and rotating a blade within the volume of tissue to slice an ovoid path through the volume of tissue; and
    injecting a physiologically acceptable binding material into the disrupted volume of tissue, all without permanently removing or displacing at least 50 percent of the weight of the volume of tissue.

2. The method of claim 1, wherein the step of disrupting comprises concurrently extending and rotating the blade within the volume of tissue.

3. The method of claim 1, wherein the step of disrupting comprises introducing multiple lacerations into the volume of tissue.

4. The method of claim 1, wherein the step of disrupting comprises pulping the volume of tissue.

5. The method of claim 1, further comprising increasing a height of a vertebral body prior to finishing the step of injecting.

6. The method of claim 1, further comprising restoring a vertebral body to a normal anatomical height.

7. The method of claim 1, further comprising leaving at least 50 wt % of the disrupted volume in situ.

8. The method of claim 1, further comprising leaving at least 70 wt % of the disrupted volume in situ.

9. The method of claim 1, further comprising leaving at least 90 wt % of the disrupted volume in situ.

10. The method of claim 1, wherein the physiologically acceptable binding material comprises a polymeric cement.

11. The method of claim 1, further comprising injecting the physiologically acceptable binding material under pressure sufficient to interdigitate the material into a portion of the tissue other than the disrupted tissue.

* * * * *